United States Patent [19]
Papen et al.

[11] Patent Number: 6,079,283
[45] Date of Patent: Jun. 27, 2000

[54] METHOD FOR ASPIRATING SAMPLE LIQUID INTO A DISPENSER TIP AND THEREAFTER EJECTING DROPLETS THERETHROUGH

[75] Inventors: Roeland F. Papen, Wheaton; Richard E. Pelc, Libertyville; Nicholas S. Chibucos, Bloomingdale, all of Ill.; Wilhelm Meyer, Tostedt, Germany

[73] Assignee: Packard Instruments Comapny, Downers Grove, Ill.

[21] Appl. No.: 09/012,174

[22] Filed: Jan. 22, 1998

Related U.S. Application Data

[63] Continuation of application No. 08/656,455, May 31, 1996, abandoned.

[51] Int. Cl.[7] .............................. B01L 3/02; B67D 5/08
[52] U.S. Cl. .................................... 73/864.11; 73/864.22; 436/180
[58] Field of Search ............................ 436/180; 422/100, 422/930; 73/864.01, 864.22, 864.11, 864.12, 1, 74; 222/36, 37, 38, 55, 57, 63, 64, 66, 148, 333; 901/16, 41, 43, 46

[56] References Cited

U.S. PATENT DOCUMENTS

| | | | |
|---|---|---|---|
| 3,427,480 | 2/1969 | Robinson | 310/8.1 |
| 3,452,360 | 6/1969 | Williamson | 346/140 |
| 3,501,064 | 3/1970 | Gaumer | 422/930 X |
| 3,507,269 | 4/1970 | Berry | 128/2 |
| 3,512,173 | 5/1970 | Darmouth | 346/75 |

(List continued on next page.)

FOREIGN PATENT DOCUMENTS

| | | |
|---|---|---|
| 0 012 821 | 11/1979 | European Pat. Off. ........ G06K 15/02 |
| 0 024 230 | 2/1981 | European Pat. Off. .......... B01L 3/02 |
| 0 119 573 | 9/1984 | European Pat. Off. .......... C12M 1/26 |
| 0 169 071 | 1/1986 | European Pat. Off. . |
| 0 268 237 | 5/1988 | European Pat. Off. . |
| 0 508 531 | 10/1992 | European Pat. Off. . |
| 0 545 284 | 6/1996 | European Pat. Off. . |
| 0 781 987 A2 | 7/1997 | European Pat. Off. ........ G01N 21/03 |
| 0781 987 A3 | 7/1997 | European Pat. Off. . |
| 55-79167 | 12/1978 | Japan .................. B41J 3/04 |
| 1-150549 | 6/1989 | Japan .................. B41J 3/04 |
| 249861 | 9/1994 | Japan . |
| WO 92/18608 | 10/1992 | WIPO .............. C12M 1/26 |
| WO 94/06568 | 3/1994 | WIPO .............. B05B 5/16 |
| WO 95/01559 | 1/1995 | WIPO .............. G01N 1/28 |
| WO 97/16251 | 5/1997 | WIPO .............. B01L 3/02 |

OTHER PUBLICATIONS

Patent Abstracts of Japan (JP 012 34114).

Boillat et al., "A Differential Pressure Liquid Flow Sensor for Flow Regulation and Dosing Systems," Proceedings IEEE, Micro Electro Mechanical Systems, MEMS, '95 Amsterdam pp. 350–352.

Schober, A., et al., "Accurate High–Speed Liquid Handling of Very Small Biological Samples," BioTechniques, vol. 15, No. 2 (1993), p. 324–329.

Plunkett, Matthew J. et al., "Combinatorial Chemistry and New Drugs," Scientific American, Apr. 1997, pp. 69–73.

Microdrop Instruction Manual, Microdrop Gesellschaft für Mikrodosiersysteme mbH, MD–K–130SP/140H/135/150 and Drive electronics MD–E–204, May 1994 cases & pp. 1–9.

(List continued on next page.)

*Primary Examiner*—Thomas P. Noland
*Attorney, Agent, or Firm*—Jenkens & Gilchrist

[57] ABSTRACT

A low volume liquid handling system is described which includes a microdispenser employing a piezoelectric transducer attached to a glass capillary, a positive displacement pump for priming and aspirating liquid into the microdispenser, controlling the pressure of the liquid system, and washing the microdispenser between liquid transfers, and a pressure sensor to measure the liquid system pressure and produce a corresponding electrical signal. The pressure signal is used to verify and quantify the microvolume dispensed and is used to perform automated calibration and diagnostics on the microdispenser.

12 Claims, 4 Drawing Sheets

U.S. PATENT DOCUMENTS

| | | | |
|---|---|---|---|
| 3,549,328 | 12/1970 | Kilburn | 23/253 |
| 3,666,421 | 5/1972 | Price | 23/253 |
| 3,683,212 | 8/1972 | Zoltan | 310/8.3 |
| 3,711,252 | 1/1973 | Roy | 23/253 |
| 3,741,726 | 6/1973 | Mitchell et al. | 436/180 |
| 3,772,154 | 11/1973 | Isenberg et al. | 435/33 |
| 3,798,961 | 3/1974 | Flambard et al. | |
| 3,831,845 | 8/1974 | Pacht | 239/76 |
| 3,832,579 | 8/1974 | Arndt | 310/8.1 |
| 3,838,012 | 9/1974 | Higgens | 195/127 |
| 3,859,169 | 1/1975 | O'Driscoll et al. | 195/63 |
| 3,902,083 | 8/1975 | Zoltan | 310/8.1 |
| 3,946,398 | 3/1976 | Kyser et al. | 346/1 |
| 3,958,249 | 5/1976 | DeMaine et al. | 346/1 |
| 3,964,871 | 6/1976 | Hochstrasser | 23/253 |
| 3,975,162 | 8/1976 | Renn | 23/253 |
| 3,985,467 | 10/1976 | Lefferson | 417/20 |
| 3,994,423 | 11/1976 | Burg | 222/420 |
| 3,996,006 | 12/1976 | Pagano | 23/253 |
| 4,038,570 | 7/1977 | Durley, III | 310/8.1 |
| 4,046,513 | 9/1977 | Johnson | 23/253 |
| 4,084,165 | 4/1978 | Skafvensted et al. | 346/140 R |
| 4,087,332 | 5/1978 | Hansen | 195/127 |
| 4,140,018 | 2/1979 | Maldarelli et al. | 73/864.22 X |
| 4,193,009 | 3/1980 | Durley, III | 310/323 |
| 4,216,245 | 8/1980 | Johnson | 427/2 |
| 4,223,558 | 9/1980 | Schmider et al. | |
| 4,234,103 | 11/1980 | Strobl, Jr. et al. | 222/83.5 |
| 4,241,406 | 12/1980 | Kennedy et al. | 364/518 |
| 4,278,983 | 7/1981 | Halasz | 346/140 R |
| 4,293,867 | 10/1981 | Isayama | 346/140 R |
| 4,308,546 | 12/1981 | Halasz | 346/140 R |
| 4,341,310 | 7/1982 | Sangiovanni et al. | 209/638 |
| 4,366,490 | 12/1982 | DeBonte et al. | 346/140 R |
| 4,410,020 | 10/1983 | Lorenz | 141/65 |
| 4,418,356 | 11/1983 | Reece | 346/140 R |
| 4,426,031 | 1/1984 | Halasz | 228/121 |
| 4,447,375 | 5/1984 | Schimmelpfennig | 264/40.5 |
| 4,459,267 | 7/1984 | Bunce et al. | 73/864.11 X |
| 4,492,322 | 1/1985 | Hieftje et al. | 222/420 |
| 4,498,088 | 2/1985 | Kanayama | 346/140 R |
| 4,503,012 | 3/1985 | Starr | 422/100 |
| 4,504,845 | 3/1985 | Kattner et al. | 346/140 R |
| 4,512,722 | 4/1985 | Mouton | 417/63 |
| 4,514,743 | 4/1985 | Roschlein et al. | 346/140 R |
| 4,518,974 | 5/1985 | Isayama | 346/140 R |
| 4,530,463 | 7/1985 | Hiniker et al. | 239/71 |
| 4,539,575 | 9/1985 | Nilsson | 346/140 R |
| 4,548,825 | 10/1985 | Voss et al. | 426/383 |
| 4,550,325 | 10/1985 | Viola | 346/140 R |
| 4,574,850 | 3/1986 | Davis | 73/864.24 X |
| 4,600,928 | 7/1986 | Braun et al. | 346/1.1 |
| 4,646,104 | 2/1987 | Braun | 346/1.1 |
| 4,651,161 | 3/1987 | Rich et al. | 346/1.1 |
| 4,672,398 | 6/1987 | Kuwabara et al. | 346/140 R |
| 4,681,741 | 7/1987 | Hanaway | 422/100 |
| 4,682,710 | 7/1987 | Turner, Jr. et al. | 222/63 |
| 4,691,850 | 9/1987 | Kirschmann et al. | 222/642 |
| 4,695,852 | 9/1987 | Scardovi | 346/140 R |
| 4,701,754 | 10/1987 | Provonchee | 340/815.03 |
| 4,777,832 | 10/1988 | Prodosmo et al. | 73/863.02 |
| 4,877,745 | 10/1989 | Hayes et al. | 436/166 |
| 4,934,419 | 6/1990 | Lamont et al. | 141/94 |
| 4,976,259 | 12/1990 | Higson et al. | 128/200.18 |
| 5,055,263 | 10/1991 | Meltzer | 422/65 |
| 5,059,393 | 10/1991 | Quenin et al. | 422/64 |
| 5,072,235 | 12/1991 | Slowik et al. | 346/1.1 |
| 5,141,871 | 8/1992 | Kureshy et al. | 436/47 |
| 5,225,750 | 7/1993 | Higuchi et al. | 318/280 |
| 5,229,679 | 7/1993 | Higuchi et al. | 310/328 |
| 5,232,664 | 8/1993 | Krawzak et al. | 422/64 |
| 5,275,951 | 1/1994 | Chow et al. | 73/864.24 X |
| 5,297,734 | 3/1994 | Toda | 239/102.2 |
| 5,306,510 | 4/1994 | Meltzer | 422/65 |
| 5,334,353 | 8/1994 | Battner | 422/100 |
| 5,356,034 | 10/1994 | Schlumberger | 222/61 |
| 5,365,783 | 11/1994 | Zwefel | 73/304 X |
| 5,457,527 | 10/1995 | Manns et al. | 356/246 |
| 5,485,828 | 1/1996 | Hauser | 128/200.16 |
| 5,525,515 | 6/1996 | Blattner | 436/49 |
| 5,529,754 | 6/1996 | Bonacina et al. | 422/82.01 |
| 5,630,793 | 5/1997 | Rowe | 604/20 |
| 5,665,312 | 9/1997 | Sperber et al. | 436/180 X |
| 5,693,016 | 12/1997 | Gumaste et al. | 604/131 |
| 5,763,278 | 6/1998 | Sickinger et al. | 436/180 |
| 5,785,926 | 7/1998 | Seubert et al. | 73/864.11 X |
| 5,927,547 | 7/1999 | Paper et al. | 222/57 |

OTHER PUBLICATIONS

Microdrop Instruction Manual, Microdrop Gesselschaft für Mikrodosiersysteme mbH, AD–E–130, Sep. 1995 12 pages.

"Microdosing in the picoliter range with piezo technology" sales brochure from Microdrop Gesellschaft für Mickrodosiersysteme mbH, Oct., 1995 23 pages.

Joshi and Sacks "Circular Slot Burner–Droplet Generator System for High–Temperature Reaction and Vapor Transport Studies", pp. 1781–1785, Analytical Chemistry, vol. 51, No. 11, Sep. 1979.

Holcombe, Eklund & Grice, "Vaporization and Atomization of Large Particles in an Acetylene/Air Flame", pp. 2097–2103, Analytical Chemistry, vol. 50, No. 14, Dec. 1978.

Buehner, et al., "Application of Ink Jet Technology to a Word Processing Output Printer", pp. 1–9, IBM J. Res. Develop.

Curry, Portig, "Scale Model of an Ink Jet", pp. 10–20, IBM J. Res. Develop.

Pimbley "Satellite Droplet Formation in a Liquid Jet" pp. 21–30, Satellite Formation, IBM J. Res. Develop.

Twardeck "Effect of Parameter Variations on Drop Placement in an Electrostatic Ink Jet Printer" pp. 31–36, IBM J. Res. Develop.

Filmore et al. Drop Charging and Deflection in an Electrostatic Ink Jet Printer, pp. 37–47, IBM J. Res. Develop.

Lee "Boundary Layer Around a Liquid Jet" pp. 48–51, IBM J. Res. Develop.

Carmichael, "Controlling Print Height in an Ink Jet Printer" pp. 52–55, IBM J. Res. Develop.

Levanoni, "Study of Fluid Flow through Scaled–up Ink Jet Nozzles" pp. 56–68, IBM J. Res. Develop.

Ashley et al. "Development and Characterization of Ink for an Electrostatic Ink Jet Printer" pp. 69–74, IBM J. Res. Develop.

Beach et al., "Materials Selection for an Ink Jet Printer" pp. 75–86, IBM J. Res. Develop.

METHOD FOR ASPIRATING SAMPLE LIQUID INTO A DISPENSER TIP AND THEREAFTER EJECTING DROPLETS THERETHROUGH

This application is a continuation of Ser. No. 08/656,455 filed May 31, 1996 and now abandoned.

FIELD OF THE INVENTION

The present invention relates to an apparatus and process for controlling, dispensing and measuring small quantities of fluid. More specifically, the present invention senses pressure changes to ascertain and confirm fluid volume dispensed and proper system functioning.

BACKGROUND OF THE INVENTION

Advances in industries employing chemical and biological processes have created a need for the ability to accurately and automatically dispense small quantities of fluids containing chemically or biologically active substances for commercial or experimental use. Accuracy and precision in the amount of fluid dispensed is important both from the standpoint of causing a desired reaction and minimizing the amount of materials used.

Equipment for dispensing microvolumes of liquid have been demonstrated with technologies such as those developed for ink jet applications. However, ink jet equipment has the advantage of operating with a particular ink (or set of inks) of known and essentially fixed viscosity and other physical properties. Thus, because the properties of the ink being used are known and fixed, automatic ink jet equipment can be designed for the particular ink specified. Direct use of ink jet technology with fluids containing a particular chemical and biological substance of interest ("transfer liquid") is more problematic. Such transfer liquids have varying viscosity and other physical properties that make accurate microvolume dispensing difficult. Automatic microvolume liquid handling systems should be capable of handling fluids of varying viscosity and other properties to accommodate the wide range of substances they must dispense. Another aspect of this problem is the need to accommodate accurately dispensing smaller and smaller amounts of transfer liquid. Especially in the utilization and test of biological materials, it is desirable to reduce the amount of transfer liquid dispensed in order to save costs or more efficiently use a small amount of material available. It is often both desirable and difficult to accurately dispense microvolumes of transfer liquid containing biological materials. Knowing the amount of transfer liquid dispensed in every ejection of transfer liquid would be advantageous to an automated system.

Another difficulty with dispensing microvolumes of transfer liquid arises due to the small orifices, e.g., 20–80 micrometers in diameter, employed to expel a transfer liquid. These small orifice sizes are susceptible to clogging. Further exacerbating the clogging problem are the properties of the substances sometimes used in the transfer liquid. Clogging of transfer liquid substances at the orifice they are expelled from, or in other parts of the dispenser, can halt dispensing operations or make them far less precise. Therefore, it would be desirable to be able to detect when such conditions are occurring, and to be able to automatically recover from these conditions. Failure of a microvolume dispenser to properly dispense transfer fluid can also be caused by other factors, such as air or other compressible gases being in the dispensing unit. It would be desirable to detect and indicate when a microvolume dispenser is either not dispensing at all, or not dispensing the desired microvolume ("misfiring").

In order to achieve an automated microvolume dispensing system it would be desirable to ensure in realtime that the transfer liquid is within some given range of relevant system parameters in order to rapidly and accurately dispense transfer liquid droplets of substantially uniform size. Because industry requires rapid dispensing of microvolume amounts of transfer liquid, it is desirable to be able to ascertain transfer liquid volume dispensed, and to be able to detect and recover from dispensing problems in realtime.

SUMMARY OF THE INVENTION

It is a primary object of the present invention to provide a microvolume liquid handling system which is capable of accurately verifying microvolume amounts of transfer liquid dispensed by sensing a corresponding change in pressure in the microvolume liquid handling system.

It is also an object of the present invention to provide a microvolume liquid handling system which can accurately measure an amount of dispensed liquid regardless of transfer liquid properties such as viscosity.

It is another object of the present invention to provide a microvolume liquid handling system which can transfer microvolume quantities of fluids containing chemically or biologically active substances.

It is still another object of the present invention to provide a microvolume liquid handling system which senses pressure changes associated with clogging and misfiring to indicate such improper operation.

It is yet another object of the present invention to provide a microvolume liquid handling system which can verify that the transfer liquid is maintained within a given range of negative pressure (with respect to ambient atmospheric pressure) in order to accurately dispense microvolume amounts of transfer liquid and optimize the operation of the microdispenser.

Other objects and advantages of the present invention will be apparent from the following detailed description.

Accordingly, the foregoing objectives are realized by providing a microvolume liquid handling system which includes a positive displacement pump operated by a stepper motor, a piezoresistive pressure sensor, and an electrically controlled microdispenser that utilizes a piezoelectric transducer bonded to a glass capillary. The microdispenser is capable of rapidly and accurately dispensing sub-nanoliter ("nl") sized droplets by forcibly ejecting the droplets from a small nozzle.

To provide the functionality of an automated liquid handling system, the microdispenser is mounted onto a 3-axis robotic system that is used to position the microdispenser at specific locations required to execute the desired liquid transfer protocol.

The present invention includes a system liquid and a transfer liquid in the dispensing system separated by a known volume of air ("air gap") which facilitates measuring small changes in pressure in the system liquid that correlate to the volume of transfer liquid dispensed. The transfer liquid contains the substances being dispensed, while in one preferred embodiment the system liquid is deionized water. Each time a droplet in the microvolume dispensing range is dispensed, the transfer liquid will return to its prior position inside the microdispenser because of capillary forces, and the air gap's specific volume will be increased corresponding to the amount of transfer liquid dispensed. This has the effect of decreasing pressure in the system liquid line which is measured with a highly sensitive piezoresistive pressure sensor. The pressure sensor transmits an electric signal to control circuitry which converts the electric signal into a digital form and generates an indication of the corresponding volume of transfer liquid dispensed. An advantage of the present invention is its insensitivity to the viscosity of the transfer liquid. This is because the pressure change in the system liquid corresponds to the microvolume dispensed, without being dependent on the dispensed fluid viscosity. The present invention possesses unique capabilities in microvolume liquid handling. This system is capable of automatically sensing liquid surfaces, aspirating liquid to be transferred, and then dispensing small quantities of liquid with high accuracy, speed and precision. The dispensing is accomplished without the dispenser contacting the destination vessel or contents. A feature of the present invention is the capability to positively verify the microvolume of liquid that has been dispensed during realtime operation.

Figure 1:
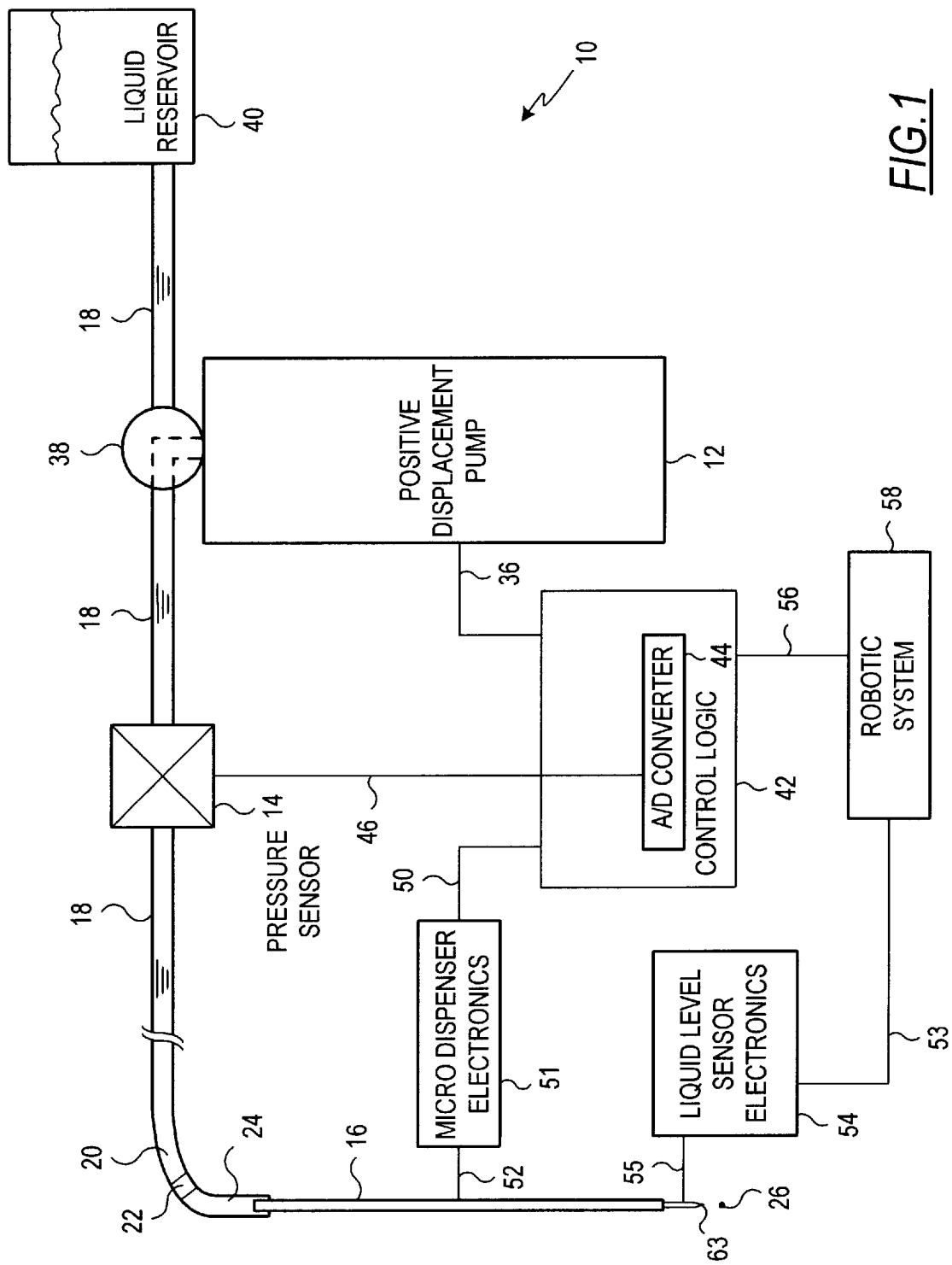
FIG. 1 is a block diagram of the a microvolume liquid handling system embodying the present invention.

While the invention is susceptible to various modifications and alternative forms, specific embodiments thereof have been shown by way of example in the drawings and will herein be described in detail. It should be understood, however, that it is not intended to limit the invention to the particular forms disclosed. On the contrary, the intention is to cover all modifications, equivalents, and alternatives falling within the spirit and scope of the invention as defined by the appended claims.

DETAILED DESCRIPTION OF THE INVENTION

Turning now to the drawings and referring first to FIG. 1, a microvolume liquid handling system 10 is illustrated. The microvolume liquid handling system 10 includes a positive displacement pump 12, a pressure sensor 14 and a microdispenser 16. Tubing 18 connects the positive displacement pump 12 to the pressure sensor 14 and the pressure sensor 14 to the microdispenser 16. The positive displacement pump 12 moves a system liquid 20 through the pressure sensor 14 and the microdispenser 16. After the system 10 is loaded with system liquid 20, an air gap 22 of known volume, then an amount of transfer liquid 24, are drawn into the microdispenser 16 in a manner described below. The transfer liquid 24 contains one or more biologically or chemically active substances of interest. In one preferred embodiment the microdispenser 16 expels (or synonymously, "shoots") sub-nanoliter size individual droplets 26 which are very reproducible. The expelled droplets 26 of transfer liquid 24 are on the order of 0.45 nanoliters per droplet 26 in one preferred embodiment, but they can be as small as 5 picoliters. For example, if one desires to expel a total of 9 nanoliters of transfer liquid 24, then the microdispenser 16 will be directed to expel 20 droplets 26. Droplet 26 size can be varied by varying the magnitude and duration of the electrical signal applied to the microdispenser 16. Other factors affecting droplet size include: the size of the nozzle opening at the bottom of the microdispenser, the pressure at the microdispenser inlet, and properties of the transfer liquid.

Figure 2:
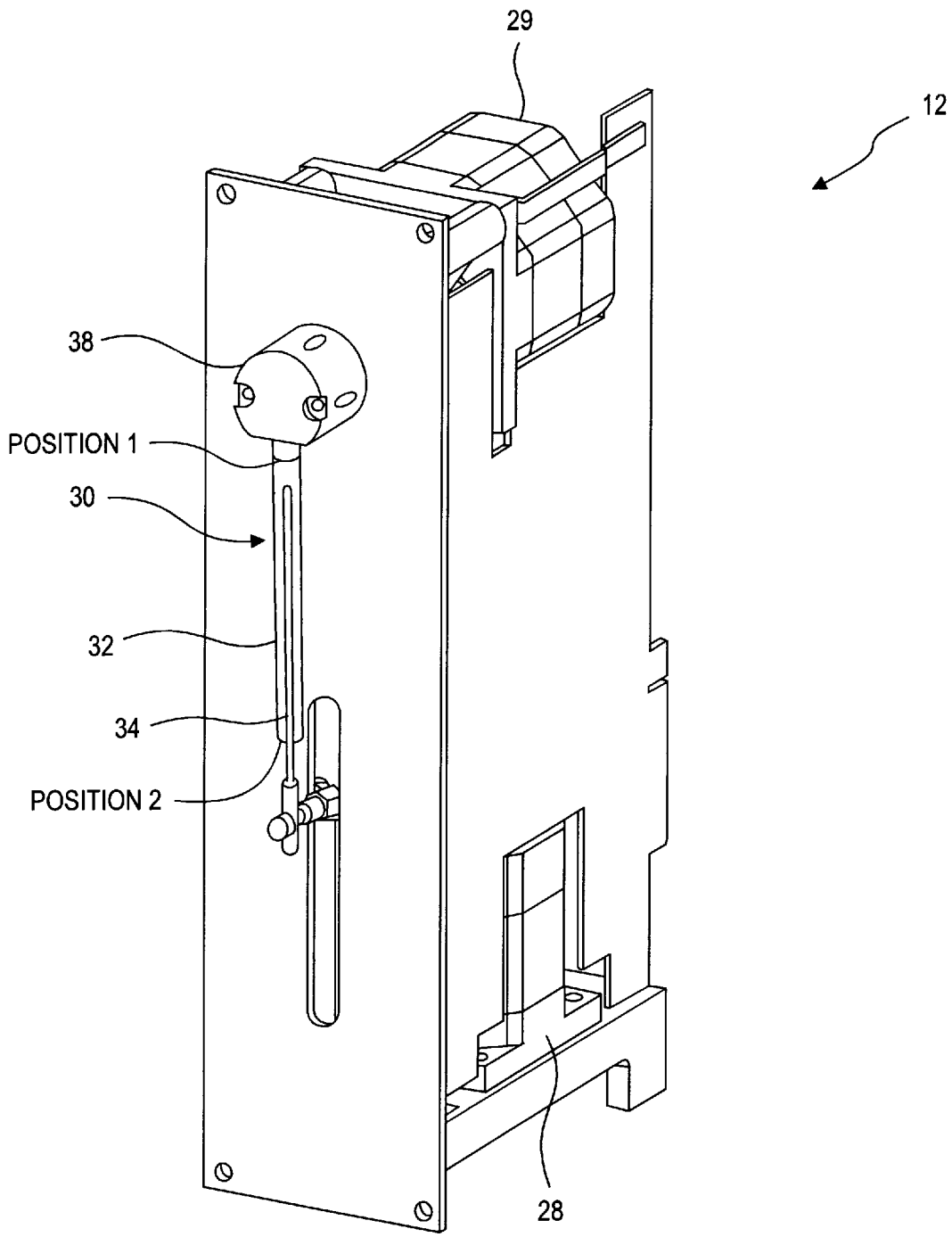
FIG. 2 is a schematic of a positive displacement pump.

Referring now to FIGS. 1 and 2, in one preferred embodiment the positive displacement pump 12 is a XL 3000 Modular Digital Pump manufactured by Cavro Scientific Instruments, Inc., 242 Humboldt Court, Sunnyvale, Calif. 94089. The positive displacement pump 12 includes stepper motor 28 and stepper motor 29, and a syringe 30. The syringe 30 includes a borosilicate glass tube 32 and a plunger 34 which is mechanically coupled through a series of gears and a belt (not shown) to the stepper motor 28. Stepper motor 28 motion causes the plunger 34 to move up or down by a specified number of discrete steps inside the glass tube 32. The plunger 34 forms a fluidtight seal with the glass tube 32. In one preferred embodiment syringe 30 has a usable capacity of 250 microliters which is the amount of system liquid 20 the plunger 34 can displace in one full stroke. Depending on the selected mode of operation, the stepper motor 28 is capable of making 3,000 or 12,000 discrete steps per plunger 34 full stroke. In one preferred embodiment the stepper motor 28 is directed to make 12,000 steps per full plunger 34 stroke with each step displacing approximately 20.83 nanoliters of system liquid 20. In one preferred embodiment the system liquid 20 utilized is deionized water.

Digitally encoded commands cause the stepper motor 28 within the positive displacement pump 12 to aspirate discrete volumes of liquid into the microdispenser 16, wash the microdispenser 16 between liquid transfers, and to control the pressure in the system liquid 20 line for microvolume liquid handling system 10 operation. The positive displacement pump 12 is also used to prime the system 10 with system liquid 20 and to dispense higher volumes of liquid through the microdispenser 16, allowing dilute solutions to be made. The positive displacement pump 12 can also work directly with transfer liquid 24. Thus, if desired, transfer liquid 24 can be used as system liquid 20 throughout the microvolume liquid handling system 10.

To prime the microvolume liquid handling system 10, the control logic 42 first directs a 3-axis robotic system 58 through electrical wire 56 to position the microdispenser 16 over a wash station contained on the robotic system 58. In one preferred embodiment the microvolume liquid handling system 10 includes, and is mounted on, a 3-axis robotic system is a MultiPROBE CR10100, manufactured by Packard Instrument Company, Downers Grove, Ill. The positive displacement pump 12 includes a valve 38 for connecting a system liquid reservoir 40 to the syringe 30. An initialization control signal is transmitted through the electrical cable 36 to the pump 12 by control logic 42 which causes the valve 38 to rotate connecting the syringe 30 with the system fluid reservoir 40. The control signal also causes the stepper motor 28 to move the plunger 34 to its maximum extent up (Position 1 in FIG. 2) into the borosilicate glass tube 32. The next command from the control logic 42 causes the stepper motor 28 to move the plunger 34 to its maximum extent down (Position 2 in FIG. 2) inside the tube 32, to extract system liquid 20 from the system reservoir 40. Another command from the control logic 42 directs the valve 38 to rotate again, causing the syringe 30 to be connected with the tubing 18 connected to the pressure sensor 14. In one preferred embodiment the tubing 18 employed in the microvolume liquid handling system 10 is Natural Color Teflon Tubing made by Zeus Industrial Products, Inc., Raritan, N.J., with an inner diameter of 0.059 inches and an outer diameter of 0.098 inches. The next command from the control logic 42 to the positive displacement pump 12 causes the system liquid 20 inside of the syringe 30 to be pushed into the microvolume liquid handling system 10 towards the pressure sensor 14. Because the microvolume liquid handling system 10 typically requires about 4 milliliters of system fluid to be primed, the sequence of steps described above must be repeated about 16 times in order to completely prime the microvolume liquid handling system 10.

The control logic 42 receives signals from the pressure sensor 14 through an electrical line 46. The signals are converted from an analog form into a digital form by an A/D (analog to digital) converter 44 and used by the control logic 42 for processing and analysis. In one preferred embodiment the A/D conversion is a PC-LPM-16 Multifunction I/O Board manufactured by National Instruments Corporation, Austin, Tex. At various points in the liquid transfer process described herein, the control logic 42 receives signals from the pressure transducer 14, and sends command signals to the pump 12, microdispenser electronics 51, and the 3-axis robotic system 58. Within the control logic 42 are the encoded algorithms that sequence the hardware (robotic system 58, pump 12, and microdispenser electronics 51) for specified liquid transfer protocols as described herein. Also within the control logic 42 are the encoded algorithms that process the measured pressure signals to: verify and quantify microdispenses, perform diagnostics on the state of the microvolume liquid handling system, and automatically perform a calibration of the microdispenser for any selected transfer liquid 24.

The pressure sensor 14 senses fluctuations in pressure associated with priming the microvolume liquid handling system 10, aspirating transfer liquid 24 with pump 12, dispensing droplets 26 with microdispenser 16, and washing of microdispenser 16 using pump 12. In one preferred embodiment the pressure sensor 14 is a piezoresistive pressure sensor part number 26PCDFG6G, from Microswitch, Inc., a Division of Honeywell, Inc., 11 West Spring Street, Freeport, Ill. 61032. Also included with the pressure sensor 14 in the block diagram in FIG. 1 is electrical circuitry to amplify the analog pressure signal from the pressure sensor. The pressure sensor 14 converts pressure into electrical signals which are driven to the A/D converter 44 and then used by the control logic 42. For example, when the microvolume liquid handling system 10 is being primed, the pressure sensor 14 will send electrical signals which will be analyzed by the control logic 42 to determine whether they indicate any problems within the system such as partial or complete blockage in the microdispenser 16.

Once the microvolume liquid handling system 10 is primed, the control logic 42 sends a signal through electrical wire 56 which instructs the robotic system 58 to position the microdispenser 16 in air over the transfer liquid 24. The control logic 42 instructs stepper motor 28 to move the plunger 34 down, aspirating a discrete quantity of air (air gap), e.g., 50 microliters in volume into the microdispenser 16. The control logic 42 then instructs the robotic system 58 to move the microdispenser 16 down until it makes contact with the surface of the transfer liquid 24 (not shown) is made. Contact of the microdispenser 16 with the surface of the transfer liquid 24 is determined by a capacitive liquid level sense system (U.S. Pat. No. 5,365,783). The microdispenser is connected by electrical wire 55 to the liquid level sense electronics 54. When the liquid level sense electronics 54 detects microdispenser 16 contact with transfer liquid 24 surface, a signal is sent to the robotic system 58 through electrical wire 53 to stop downward motion.

The control logic 42 next instructs the pump 12 to move the plunger 34 down in order to aspirate transfer liquid 24 into the microdispenser 16. The pressure signal is monitored by control logic 42 during the aspiration to ensure that the transfer liquid 24 is being successfully drawn into the microdispenser 16. If a problem is detected, such as an abnormal drop in pressure due to partial or total blockage of the microdispenser, the control logic 24 will send a stop movement command to the pump 12. The control logic 24 will then proceed with an encoded recovery algorithm. Note that transfer liquid 24 can be drawn into the microvolume liquid handling system 10 up to the pressure sensor 14 without threat of contaminating the pressure sensor 14. Additional tubing can be added to increase transfer liquid 24 capacity. Once the transfer liquid 24 has been aspirated into the microdispenser 16, the control logic 42 instructs the robotic system 58 to reposition the microdispenser 16 above the chosen target, e.g., a microtitre plate.

In one preferred embodiment the microdispenser 16 is the MD-K-130 Microdispenser Head manufactured by Microdrop, GmbH, Muhlenweg 143, D22844 Norderstedt, Germany.

Figure 3:
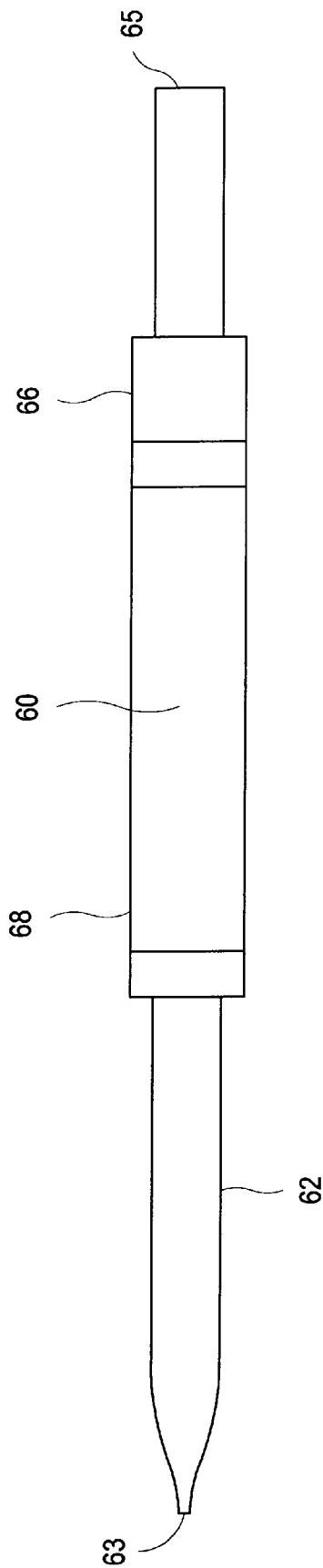
FIG. 3 is an illustration of a microdispenser and a piezoelectric transducer.

As illustrated in FIG. 3, the microdispenser 16 consists of a piezoceramic tube 60 bonded to a glass capillary 62. The piezoceramic tube has an inner electrode 66 and an outer electrode 68 for receiving analog voltage pulses which cause the piezoceramic tube to constrict. Once the glass capillary 62 has been filled with transfer liquid 24, the control logic 42 directs the microdispenser electronics 51 by electrical wire 50 to send analog voltage pulses to the piezoelectric transducer 60 by electrical wire 52. In one preferred embodiment the microdispenser electronics 51 is the MD-E-201 Drive Electronics manufactured by Microdrop, GmbH, Muhlenweg 143, D-22844 Norderstedt, Germany. The microdispenser electronics 51 control the magnitude and duration of the analog voltage pulses, and also the frequency at which the pulses are sent to the microdispenser 16. Each voltage pulse causes a constriction of the piezoelectric transducer 60, which in turn deforms the glass capillary 62. The deformation of the glass capillary 62 produces a pressure wave that propagates through the transfer liquid 24 to the microdispenser nozzle 63 where one droplet 26 of transfer liquid 24 is emitted under very high acceleration. The size of these droplets 26 has been shown to be very reproducible. The high acceleration of the transfer liquid 24 minimizes or eliminates problems caused by transfer liquid 24 surface tension and viscosity, allowing extremely small droplets 26 to be expelled from the nozzle, e.g., as small as 5 picoliter droplets 26 have been demonstrated. Use of the microdispenser 16 to propel droplets 26 out of the nozzle also avoids problems encountered in a liquid transfer technique called touchoff. In the touchoff technique, a droplet 26 is held at the end of the nozzle and is deposited onto a target surface by bringing that droplet 26 into contact with the target surface while it is still hanging off of the microdispenser 16. Such a contact process is made difficult by the surface tension, viscosity and wetting properties of the microdispenser 16 and the target surface which lead to unacceptable volume deviations. The present invention avoids the problems of the contact process because the droplets 26 are expelled out of the microdispenser 16 at a velocity of several meters per second. The total desired volume is dispensed by the present invention by specifying the number of droplets 26 to be expelled. Because thousands of droplets 26 can be emitted per second from the microdispenser 16, the desired microvolume of transfer liquid 24 can rapidly be dispensed.

In one preferred embodiment, the lower section of the glass capillary 62, between the piezoelectric transducer 60 and the nozzle 63, is plated with a conductive material, either platinum or gold. This provides an electrically conductive path between the microdispenser 16 and the liquid level sense electronics 54. In one preferred embodiment the glass capillary 62 has an overall length of 73 millimeters, and the nozzle 63 has an internal diameter of 75 micrometers.

Figure 4:
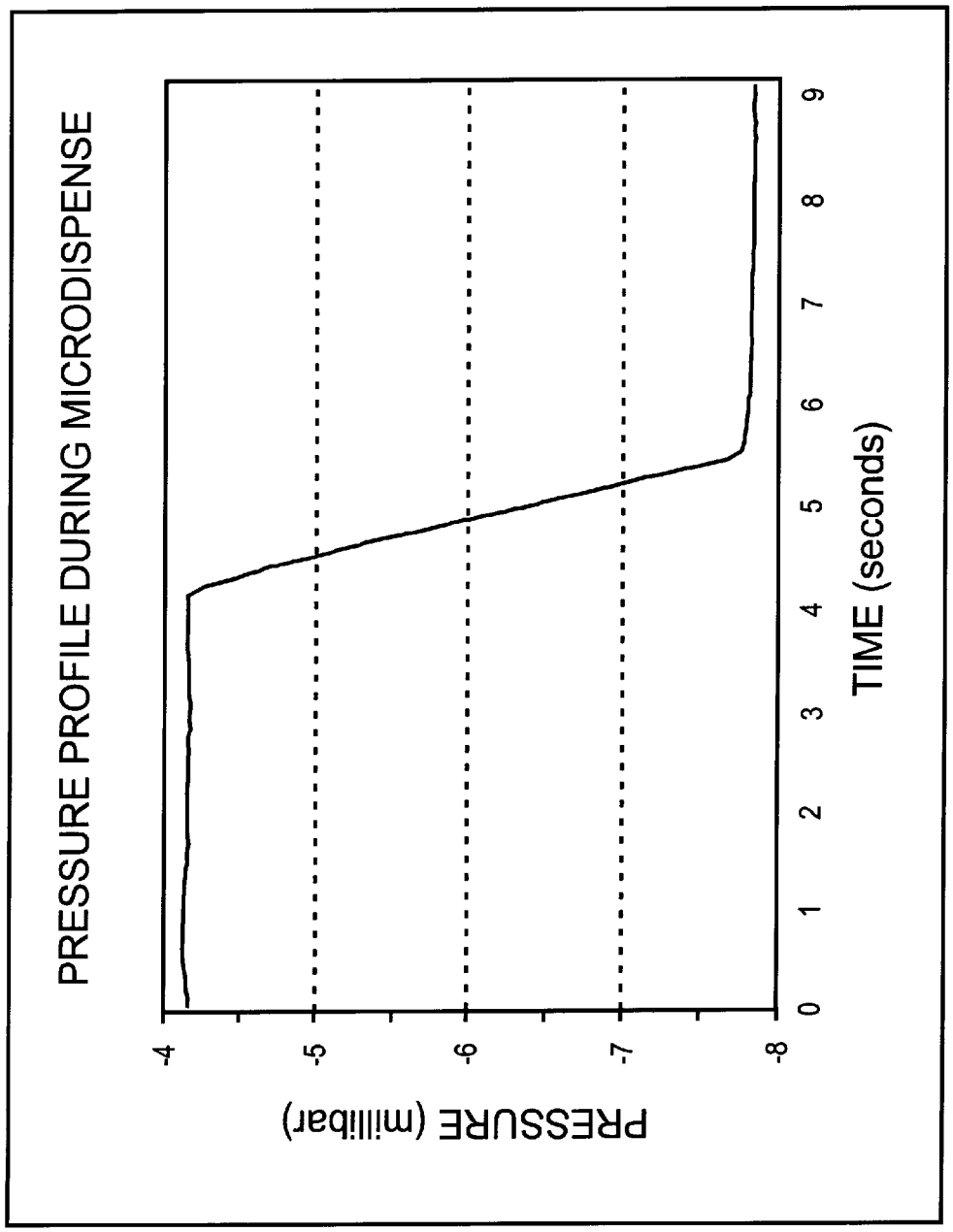
FIG. 4 is a graph depicting the system line pressure during a microdispenser dispense.

To dispense microvolume quantities of transfer liquid 24, analog voltage pulses are sent to the microdispenser 16, emitting droplets 26 of liquid. Capillary forces acting on the transfer liquid 24 replace the volume of transfer liquid 24 emitted from the microdispenser 16 with liquid from the tubing 18. However, since the transfer liquid-air gap-system liquid column terminates at a closed end in the positive displacement pump 12, there is a corresponding drop in the system liquid 20 line pressure as the air gap 22 is expanded. This is illustrated in FIG. 4 which depicts the pressure profile measured during a microdispense of 500 nanoliters. Important to the present invention, the magnitude of the pressure drop is a function of the size of the air gap 22 and the volume of the liquid dispensed.

With an air gap 22 of known volume, the pressure change as detected by the pressure sensor 14 relates to the volume dispensed. Thus, the control logic 42 determines from the pressure change measured by the pressure sensor 14, the volume of transfer liquid 24 that was dispensed. In one preferred embodiment of the present invention it is preferable that the drop in pressure not exceed approximately 30 to 40 millibars below ambient pressure, depending on the properties of the transfer liquid 24. If the amount of transfer liquid 24 dispensed is sufficient to drop the pressure more than 30 to 40 millibars, the pressure difference across the microdispenser 16, i.e., between the ambient pressure acting on the nozzle 63 and the pressure at the capillary inlet 63, will be sufficient to force the transfer liquid 24 up into the tubing 18. This will preclude further dispensing. There is a maximum amount of transfer liquid 24 that can be dispensed before the control logic 42 is required to command the pump 12 to advance the plunger 34 to compensate for the pressure drop. This maximum volume is determined by the desired dispense volume and the size of the air gap 22. Conversely, the size of the air gap 22 can be selected based on the desired dispense volume so as not to produce a pressure drop exceeding 30 to 40 millibars below ambient pressure. It is also within the scope of the present invention to advance the plunger 34 while the microdispenser 16 is dispensing, thereby rebuilding system liquid 20 line pressure, so that the microdispenser 16 can operate continuously.

The change in system liquid 20 pressure is used to determine that the desired amount of transfer liquid 24 was dispensed. A second verification of the amount of transfer liquid 24 that was dispensed is made by the control logic 42 monitoring the system liquid 20 line pressure while directing the pump 12 to advance the syringe plunger 34 upwards towards Position 1. The syringe plunger 34 is advanced until the system liquid 20 line pressure returns to the initial (pre-dispense) value. By the control logic 42 tracking the displaced volume the plunger 34 moves (20.83 nanoliters per stepper motor 28 step), a second confirmation of dispensed volume is made, adding robustness to the system. The system liquid 20 line pressure is now at the correct value for the next microdispenser 16 dispense, if a multi-dispense sequence has been specified.

Once the transfer liquid 24 dispensing has been completed, the control logic 24 causes the robotic system 58 to position the microdispenser 16 over the wash station. The control logic 24 then directs pump 12 and robotic system 58 in a wash sequence that disposes of any transfer liquid 24 left in the microdispenser 16, and washes the internal surface of glass capillary 62 and the external surface in the nozzle 63 area that was exposed to transfer liquid 24. The wash fluid can either be system liquid 20 or any other liquid placed onto the deck of the robotic system 58. The wash sequence is designed to minimize cross-contamination of subsequent transfer liquids 24 with transfer liquids processed prior. Toward this end, it is also possible to enable an ultrasonic wash of the microdispenser 16. This is accomplished by the control logic 42 directing the microdispenser electronics 51 to send electrical pulses to the microdispenser at a frequency in the ultrasonic range, e.g., 12–15 kilohertz, that coincides with a resonant frequency of the microdispenser 16—transfer liquid 24 system.

In the above description of the invention, the control of the microdispenser 16 was effected by sending a specific number of electrical pulses from the microdispenser electronics 51, each producing an emitted droplet 26 of transfer liquid 24. It is also within the scope of the invention to control the microdispenser 16 by monitoring the pressure sensor 14 signal in realtime, and continuing to send electrical pulses to the microdispenser 16 until a desired change in pressure is reached. In this mode of operation, the PC-LPM-16 Multifunction I/O Board that contains the A/D converter 44 is instructed by control logic 42 to send electrical pulses to the microdispenser electronics 51. Each pulse sent by the Multifunction I/O Board results in one electrical pulse that is sent by the microdispenser electronics 51 to the microdispenser 16, emitting one droplet 26 of transfer liquid 24. The control logic 42 monitors the pressure sensor 14 signal as the microdispenser 16 dispense is in progress, and once the desired change is pressure has been attained, the control logic 42 directs the Multifunction I/O Board to stop sending electrical pulses.

This mode of operation is employed if a "misfiring" of microdispenser 16 has been detected by control logic 42.

It is also within the scope of the invention for the microvolume liquid handling system 10 to automatically determine (calibrate) the size of the emitted droplets 26 for transfer liquids 24 of varying properties. As heretofore mentioned, emitted droplet 26 size is affected by the properties of the transfer liquid 24. Therefore, it is desirable to be able to automatically determine emitted droplet 26 size so that the user need only specify the total transfer volume, and the system 10 will internally determine the number of emitted droplets 26 required to satisfy the user request. In the encoded autocalibration algorithm, once the system 10 is primed, an air gap 22 and transfer liquid 24 aspirated, the control logic 42 instructs microdispenser electronics 51 to send a specific number of electrical pulses, e.g., 1000, to the microdispenser 16. The resulting drop in pressure sensor 14 signal is used by control logic 42 to determine the volume of transfer liquid 24 that was dispensed. This dispensed volume determination is verified by the control logic 42 tracking the volume displaced by the movement of the plunger 34 to restore the system liquid 20 line pressure to the pre-dispense value.

The microvolume liquid handling system 10 illustrated is FIG. 1 depicts a single microdispenser 16, pressure sensor 14, and pump 12. It is within the spirit and scope of this invention to include embodiments of microvolume liquid handling systems that have a multiplicity (e.g., 4, 8, 96) of microdispensers 16, pressure sensors 14, and pumps 12. It is also within the spirit and scope of this invention to include embodiments of microvolume liquid handling systems that have a multiplicity of microdispensers 16, pressure sensors 14, valves 38, and one or more pumps 12.

What is claimed is:

1. A method for aspirating at least one sample liquid through a tip opening of a dispenser into the dispenser passage and ejecting droplets of said sample liquid from said passage through the tip opening, said method comprising:
 (a) providing a system liquid into a closed container communicating with said dispenser passage;
 (b) filling the dispenser passage with said system liquid;
 (c) contacting the tip opening of said dispenser passage with a first sample liquid;
 (d) moving said system liquid in said dispenser passage away from said tip opening so as to aspirate said first sample liquid into said passage;
 (e) removing said tip opening from contact with first sample liquid;
 (f) constricting the volume of said passage so as to produce and eject a droplet of said first sample liquid;
 (g) allowing the volume to return to its pre-constricted volume;
 (h) repeating steps (f) and (g) until a desired volume of the first sample liquid is ejected.

2. The method of claim 1 further comprising the steps of discharging the first sample liquid remaining in said passage after step (h); and, discharging a sufficient volume of said system liquid through said tip opening to wash said passage.

3. The method of claim 2 further comprising the step of aspirating a second sample liquid into said passage and conducting steps (c) through (h) with respect to said second sample liquid.

4. The method of claim 1 wherein the constricting step is effected using a piezoeletric transducer.

5. The method of claim 4 wherein the filling step is effected by a positive displacement pump.

6. The method of claim 5 wherein the moving step is effected by a positive displacement pump.

7. The method of claim 6 wherein the volume of the sample liquid in step (h) is in the range from 9 nanoliters to 500 nanoliters.

8. The method of claim 1 wherein the system liquid is deionized water.

9. The method of claim 1 wherein each droplet is in the range from about 0.45 nanoliters to 5 picoliters.

10. The method of claim 9 wherein the sample liquid contains one or more biologically active substances.

11. The method of claim 1 wherein the sample liquid contains one or more chemically active substances.

12. The method of claim 1 wherein the sample liquid and the system liquid are the same.

* * * * *